United States Patent
Kennedy, III et al.

(10) Patent No.: US 9,422,328 B2
(45) Date of Patent: Aug. 23, 2016

(54) ACOUSTIC BIOREACTOR PROCESSES

(71) Applicant: FloDesign Sonics, Inc., Wilbraham, MA (US)

(72) Inventors: Thomas J. Kennedy, III, Wilbraham, MA (US); Bart Lipkens, Hampden, MA (US); Louis Masi, Longmeadow, MA (US); Stanley Kowalski, III, Wilbraham, MA (US); Chris Leidel, Somerville, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 14/329,723

(22) Filed: Jul. 11, 2014

(65) Prior Publication Data

US 2014/0329997 A1    Nov. 6, 2014

Related U.S. Application Data

(63) Continuation-in-part of application No. 14/175,766, filed on Feb. 7, 2014, which is a continuation-in-part of application No. 14/026,413, filed on Sep. 13, 2013, which is a continuation-in-part of application No. 13/844,754, filed on Mar. 15, 2013.

(51) Int. Cl.
*C07K 1/14* (2006.01)
*B01D 17/04* (2006.01)
(Continued)

(52) U.S. Cl.
CPC ............. *C07K 1/145* (2013.01); *B01D 17/04* (2013.01); *B01D 17/044* (2013.01); *B01D 17/06* (2013.01);
(Continued)

(58) Field of Classification Search
CPC ...... B01D 29/115; B01D 37/00; B01D 29/52; B01D 2201/127; B01D 2201/0446; B01D 2201/0415; B01D 29/865
USPC ................ 210/748.01–748.05, 321.6–321.9; 422/20, 292, 306; 209/155, 156
See application file for complete search history.

(56) References Cited

U.S. PATENT DOCUMENTS 2,473,971 A * 6/1949 Ross .............................. 181/198
2,667,944 A   2/1954 Crites
(Continued)

FOREIGN PATENT DOCUMENTS

DE    30 27 433 A1    2/1982
EP    0 292 470 B1    11/1988
(Continued)

OTHER PUBLICATIONS

Wang, et al., "Retention and Viability Characteristics of Mammalian Cells in an Acoustically Driven Polymer Mesh," Biotechnol. Prog. 2004, pp. 384-387 (2004).
(Continued)

*Primary Examiner* — Walter D Griffin
*Assistant Examiner* — Cameron J Allen
(74) *Attorney, Agent, or Firm* — Richard M. Klein; Fay Sharpe LLP

(57) ABSTRACT

A series of multi-dimensional acoustic standing waves is set up inside a growth volume of a bioreactor. The acoustic standing waves are used to hold a cell culture in place as a nutrient fluid stream flows through the cell culture. Biomolecules produced by the cell culture are collected by the nutrient fluid stream and separated downstream of the cell culture.

20 Claims, 10 Drawing Sheets

Related U.S. Application Data

(60) Provisional application No. 61/845,531, filed on Jul. 12, 2013, provisional application No. 61/761,717, filed on Feb. 7, 2013, provisional application No. 61/611,159, filed on Mar. 15, 2012, provisional application No. 61/708,641, filed on Oct. 2, 2012, provisional application No. 61/611,240, filed on Mar. 15, 2012, provisional application No. 61/754,792, filed on Jan. 21, 2013.

(51) Int. Cl.
*B01D 17/06* (2006.01)
*B01D 43/00* (2006.01)
*B06B 1/06* (2006.01)
*C12M 1/00* (2006.01)
*C12M 1/42* (2006.01)
*B01D 21/28* (2006.01)

(52) U.S. Cl.
CPC .............. *B01D 21/283* (2013.01); *B01D 43/00* (2013.01); *B06B 1/0622* (2013.01); *C12M 29/04* (2013.01); *C12M 35/02* (2013.01); *C12M 35/04* (2013.01); *C12M 47/10* (2013.01)

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,821,838 A | 4/1989 | Chen |
| 4,878,210 A | 10/1989 | Mitome |
| 4,983,189 A | 1/1991 | Peterson et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A * | 5/1997 | Trampler et al. ........ 210/748.05 |
| 5,688,405 A | 11/1997 | Dickinson et al. |
| 5,711,888 A * | 1/1998 | Trampler et al. ........ 210/748.05 |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,679,338 B2 | 3/2014 | Rietman et al. |
| 2002/0038662 A1* | 4/2002 | Schuler et al. ................. 134/1.3 |
| 2002/0134734 A1 | 9/2002 | Campbell et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0031499 A1* | 2/2005 | Meier ........................... 422/128 |
| 2005/0196725 A1 | 9/2005 | Fu |
| 2006/0037915 A1 | 2/2006 | Strand et al. |
| 2007/0272618 A1 | 11/2007 | Gou et al. |
| 2007/0284299 A1 | 12/2007 | Xu et al. |
| 2008/0217259 A1 | 9/2008 | Siversson |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0098027 A1 | 4/2009 | Tabata et al. |
| 2009/0104594 A1* | 4/2009 | Webb ................................ 435/3 |
| 2009/0178716 A1 | 7/2009 | Kaduchak et al. |
| 2009/0194420 A1 | 8/2009 | Mariella, Jr. et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0024335 A1 | 2/2011 | Ward et al. |
| 2011/0092726 A1 | 4/2011 | Clarke |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0189732 A1 | 8/2011 | Wienand et al. |
| 2011/0262990 A1 | 10/2011 | Wang et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0267288 A1* | 10/2012 | Chen et al. .................... 209/143 |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0277316 A1 | 10/2013 | Dutra et al. |
| 2013/0284271 A1 | 10/2013 | Lipkens et al. |
| 2014/0011240 A1 | 1/2014 | Lipkens et al. |

(56) References Cited

U.S. PATENT DOCUMENTS

FOREIGN PATENT DOCUMENTS

| | | | |
|---|---|---|---|
| EP | 1 254 669 B1 | 11/2002 |
| GB | 2 420 510 A | 5/2006 |
| WO | WO 87/07178 A1 | 12/1987 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/027146 A2 | 3/2011 |
| WO | WO 2011/161463 A2 | 12/2011 |

OTHER PUBLICATIONS

International Search Report for PCT/2014/046412 dated Oct. 27, 2014.
Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2013/037404 Dated Jun. 21, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>, 2010.

* cited by examiner

ACOUSTIC BIOREACTOR PROCESSES

CROSS-REFERENCE TO RELATED APPLICATIONS

This application claims priority to U.S. Provisional Patent Application Ser. No. 61/845,531, filed on Jul. 12, 2013. This application is also a continuation-in-part of U.S. patent application Ser. No. 14/175,766, filed on Feb. 7, 2014, which claimed priority to U.S. Provisional Patent Application Ser. No. 61/761,717, filed on Feb. 7, 2013. U.S. patent application Ser. No. 14/175,766 is also a continuation-in-part of U.S. patent application Ser. No. 14/026,413, filed on Sep. 13, 2013, which claims the benefit of U.S. Provisional Patent Application Ser. No. 61/708,641, filed on Oct. 2, 2012, and which is also a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/754,792, filed Jan. 21, 2013. These applications are incorporated herein by reference in their entireties.

BACKGROUND

Growth in the field of biotechnology has been due to many factors, some of which include the improvements in the equipment available for bioreactors. Improvements in equipment have allowed for larger volumes and lower cost for the production of biologically derived materials such as monoclonal antibodies and recombinant proteins. One of the key components used in the manufacturing processes of new biologically based pharmaceuticals is the bioreactor and the ancillary processes associated therewith.

A modern bioreactor is a very complicated piece of equipment. It provides for, among other parameters, the regulation of fluid flow rates, gas content, temperature, pH and oxygen content. All of these parameters can be tuned to allow the cell culture to be as efficient as possible of producing the desired biomolecules from the bioreactor process. One process for using a bioreactor field is the perfusion process. The perfusion process is distinguished from the fed-batch process by its lower capital cost and higher throughput.

In the fed-batch process, a culture is seeded in a bioreactor. The gradual addition of a fresh volume of selected nutrients during the growth cycle is used to improve productivity and growth. The product, typically a monoclonal antibody or a recombinant protein, is recovered after the culture is harvested. Separating the cells, cell debris and other waste products from the desired product is currently performed using various types of filters for separation. Such filters are expensive and become clogged and non-functional as the bioreactor material is processed. A fed-batch bioreactor also has high start-up costs, and generally requires a large volume to obtain a cost-effective amount of product at the end of the growth cycle, and such processes include large amounts of non-productive downtime.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). However, a perfusion bioreactor requires a cell retention device to prevent escape of the culture when byproducts are being removed. These cell retention systems add a level of complexity to the perfusion process, requiring management, control, and maintenance for successful operation. Operational issues such as malfunction or failure of the cell retention equipment has previously been a problem with perfusion bioreactors. This has limited their attractiveness in the past.

BRIEF DESCRIPTION

The present disclosure relates, in various embodiments, to systems for producing biomolecules such as recombinant proteins or monoclonal antibodies, and to processes for separating these desirable products from a cell culture in a bioreactor. Generally, the bioreactor includes a device for producing multi-dimensional standing waves. The standing waves are used to hold a cell culture in place. A nutrient fluid stream is circulated through the bioreactor past the cell culture to collect biological products/biomolecules produced by the cell culture. The biomolecules can then be separated/harvested from the nutrient fluid stream away from the cell culture.

Disclosed in various embodiments is a system comprising a bioreactor. The bioreactor includes a reaction vessel, an agitator, a feed inlet, and an outlet. A growth volume within the reaction vessel is defined by at least one ultrasonic transducer and a reflector located opposite the at least one ultrasonic transducer. The at least one ultrasonic transducer is driven to produce a multi-dimensional standing wave in the reaction vessel within the growth volume.

Also disclosed herein are processes for collecting biomolecules from a cell culture, comprising: suspending the cell culture in a growth volume of the bioreactor, the bioreactor including at least one ultrasonic transducer and a reflector located opposite the at least one ultrasonic transducer, the at least one ultrasonic transducer being driven to produce a multi-dimensional acoustic standing wave that holds the cell culture in the growth volume; and flowing a nutrient fluid stream through the cell culture to collect the biomolecules.

The bioreactor may further comprise a secondary filtering system located between the growth volume and a bioreactor outlet. The secondary filtering system is activated if the multi-dimensional acoustic standing wave fails. The multi-dimensional acoustic standing wave is generally operated in resonance.

The bioreactor may have an array of elements that form the ultrasonic transducer. Alternatively or in addition, each ultrasonic transducer may produce a plurality of multi-dimensional acoustic standing waves.

In particular embodiments, the bioreactor does not include an impeller (i.e. a physical agitator) within the growth volume. The cell culture is, in particular embodiments, composed of Chinese hamster ovary (CHO) cells. The biomolecules produced thereby can be monoclonal antibodies or recombinant proteins.

The multi-dimensional acoustic standing wave may have an axial force component and a lateral force component which are of the same order of magnitude. The bioreactor can be operated as a perfusion bioreactor. The bioreactor can include a jacket that is used to regulate the temperature of the fluid in the growth volume.

In particular embodiments, the ultrasonic transducer comprises a piezoelectric material that can vibrate in a higher order mode shape. The piezoelectric material may have a square or rectangular shape.

The ultrasonic transducer may comprise: a housing having a top end, a bottom end, and an interior volume; and a crystal at the bottom end of the housing having an exposed exterior surface and an interior surface, the crystal being able to generate acoustic waves when driven by a voltage signal. In some embodiments, a backing layer contacts the interior surface of the crystal, the backing layer being made of a substantially acoustically transparent material. The substantially acoustically transparent material can be balsa wood, cork, or foam. The substantially acoustically transparent material may have a thickness of up to 1 inch. The substantially acoustically transparent material can be in the form of a lattice. In other embodiments, an exterior surface of the crystal is covered by a wear surface material with a thickness of a half wavelength or less, the wear surface material being a urethane, epoxy, or silicone coating. The exterior surface of the crystal may also have wear surface formed from a matching layer or wear plate of material adhered to the exterior surface of the crystal. The matching layer or wear plate may be composed of aluminum oxide. In yet other embodiments, the crystal has no backing layer or wear layer.

The multi-dimensional acoustic standing wave can be a three-dimensional standing wave. The reflector and/or the ultrasonic transducer may have a non-planar surface.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
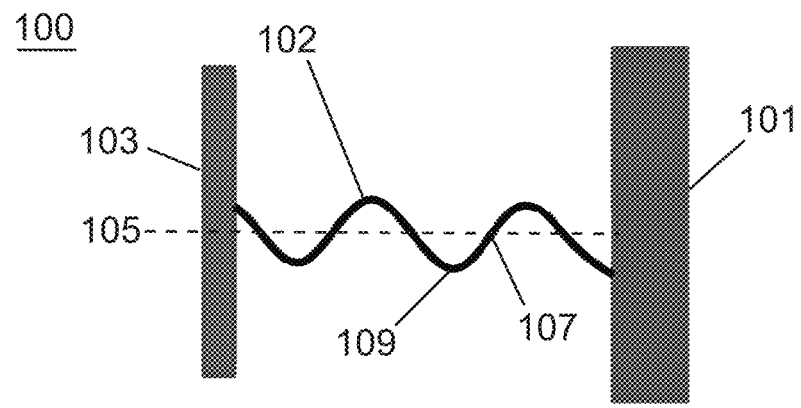
FIG. 1 illustrates a single standing acoustic wave generated by an ultrasonic transducer and a reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

The term "agitator" is used herein to refer to any device or system which can be used to cause mixing of a fluid volume, such that material in the fluid volume is dispersed and becomes more homogeneous. The term "impeller" is used to refer to a physical agitator, such as a blade. Examples of agitators which are not impellers may include aerators (which use air).

Bioreactors are useful for making biomolecules such as recombinant proteins or monoclonal antibodies. Very generally, cells are cultured in a bioreactor vessel with media in order to produce the desired product, and the desired product is then harvested by separation from the cells and media. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals.

Two general types of bioreactor processes exist: fed-batch and perfusion. Many factors favor the use of a perfusion bioreactor process. The capital and start-up costs for perfusion bioreactors are lower, smaller upstream and downstream capacity is required, and the process uses smaller volumes and fewer seed steps than fed-batch methods. A perfusion bioreactor process also lends itself better to development, scale-up, optimization, parameter sensitivity studies, and validation.

Recent developments in perfusion bioreactor technology also favor its use. Control technology and general support equipment is improving for perfusion bioreactors, increasing the robustness of perfusion processes. The perfusion process can now be scaled up to bioreactors having a volume up to 1000 liters (L). Better cell retention systems for perfusion bioreactors result in lower cell loss and greater cell densities than have been seen previously. Cell densities greater than 50 million cells/mL are now achievable, compared to fed-batch cell densities of around 20 million cells/mL. Lower contamination and infection rates have improved the output of perfusion bioreactors. Higher product concentrations in the harvest and better yields without significant increase in cost have thus resulted for perfusion processes.

There is a need for improved filtration processes in a fed-batch bioreactor process. There is also a need in perfusion bioreactor processes for improving retention of cells in the bioreactor while the biomolecules are continuously harvested.

Briefly, the present disclosure relates to the generation of three-dimensional (3-D) or multi-dimensional acoustic standing waves from one or more piezoelectric transducers, where the transducers are electrically or mechanically excited such that they move in a multi-excitation mode. The types of waves thus generated can be characterized as composite waves, with displacement profiles that are similar to leaky symmetric (also referred to as compressional or extensional) Lamb waves. The waves are leaky because they radiate into the water layer, which result in the generation of the acoustic standing waves in the water layer. Symmetric Lamb waves have displacement profiles that are symmetric with respect to the neutral axis of the piezoelectric element, which causes multiple standing waves to be generated in a 3-D space. Through this manner of wave generation, a higher lateral trapping force is generated than if the piezoelectric transducer is excited in a "piston" mode where only a single, planar standing wave is generated. Thus, with the same input power to a piezoelectric transducer, the 3-D or multi-dimensional acoustic standing waves can have a higher lateral trapping force which may be up to and beyond 10 times stronger than a single acoustic standing wave generated in piston mode. This can be used to hold the cell culture within a defined volume (referred to herein as a "growth volume") while the fluid contents and desired byproducts are removed.

Acoustophoresis is a low-power, no-pressure-drop, no-clog, solid-state approach to separate solids from fluids, i.e. it is used to achieve separations that are more typically performed with porous filters, but it has none of the disadvantages of filters. In particular, the present disclosure provides bioreactors that operate at the macro-scale to separate cell cultures in flowing systems with high flow rates. The bioreactor uses a high intensity three dimensional ultrasonic standing wave that results in an acoustic radiation force that is larger than the combined effects of fluid drag and buoyancy or gravity, and is therefore able to trap (i.e., hold in place) a suspended phase (i.e. cells and cell cultures) in the standing wave. The retained cells may clump or agglomerate. A nutrient fluid stream can then be flowed/circulated through the cell culture to provide nutrition and oxygenation to the cells, and to capture the biomolecules produced by the cells. The standing waves are also believed to stimulate the cell culture, so as to increase the rate of expression of the desired biomolecules. This provides a self-contained "acoustic bioreactor" where the biomolecules may be continuously harvested, and at an accelerated rate, from the cell culture. The present systems have the ability to create acoustic ultrasonic standing wave fields that can hold the cell cultures in place in a flow field with a linear velocity ranging from 0.1 mm/sec to velocities exceeding 1 cm/s.

The multi-dimensional ultrasonic acoustic standing waves can be used to trap, i.e., hold stationary, a cell culture in a fluid stream (e.g. cell culture medium or nutrient fluid stream). The scattering of the acoustic field off the cells results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the cells to the stable positions within the standing waves. When the acoustic radiation force exerted on the cell is stronger than the combined effect of fluid drag force and buoyancy/gravitational force, the cell is trapped within the acoustic standing wave field. The action of the acoustic forces on the trapped cells results in concentration, agglomeration and/or coalescence.

Generally, the 3-D or multi-dimensional acoustic standing wave(s) is operated at a voltage and frequency such that the biomolecule-producing cell culture, such as Chinese hamster ovary cells (CHO cells), the most common host for the industrial production of recombinant protein therapeutics, are held in place by the ultrasonic standing wave, i.e., remain in a stationary position. Within each nodal plane, the CHO cells are trapped in the minima of the acoustic radiation potential. Most cell types present a higher density and lower compressibility than the medium in which they are suspended, so that the acoustic contrast factor between the cells and the medium has a positive value. As a result, the axial acoustic radiation force (ARF) drives the CHO cells towards the standing wave pressure nodes. The axial component of the acoustic radiation force drives the cells, with a positive contrast factor, to the pressure nodal planes, whereas cells or other particles with a negative contrast factor are driven to the pressure anti-nodal planes. The radial or lateral component of the acoustic radiation force helps trap the cells. The radial or lateral component of the ARF is larger than the combined effect of fluid drag force and gravitational force. For small cells or emulsions the drag force $F_D$ can be expressed as:

$$\vec{F}_D = 4\pi \mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and cell velocity, $R_p$ is the particle radius, $\mu_f$ and $\mu_p$ are the dynamic viscosity of the fluid and the cells, and $\hat{\mu} = \mu_p/\mu_f$ is the ratio of dynamic viscosities. The buoyancy force $F_B$ is expressed as:

$$F_B = \frac{4}{3}\pi R_p^3 (\rho_f - \rho_p).$$

For a cell to be trapped in the ultrasonic standing wave, the force balance on the cell must be zero, and therefore an expression for lateral acoustic radiation force $F_{LRF}$ can be found, which is given by:

$$F_{LRF} = F_D + F_B.$$

For a cell of known size and material property, and for a given flow rate, this equation can be used to estimate the magnitude of the lateral acoustic radiation force.

The theoretical model that is used to calculate the acoustic radiation force is based on the formulation developed by Gor'kov.[17] The primary acoustic radiation force $F_A$ is defined as a function of a field potential U, $F_A = -\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2},$$

$$f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $\langle\ \rangle$ indicates time averaging over the period of the wave.

The lateral force of the total acoustic radiation force (ARF) generated by the ultrasonic transducers of the present disclosure is significant and is sufficient to overcome the fluid drag force at linear velocities of up to 1 cm/s and beyond. This lateral ARF can thus be used to retain cells in a particular volume of a bioreactor while the bioreactor process continues. This is especially true for a perfusion bioreactor.

In a perfusion bioreactor system, it is desirable to be able to filter and separate the cells and cell debris from the expressed materials that are in the fluid stream (i.e. cell culture media or nutrient fluid stream). The expressed materials are composed of biomolecules such as recombinant proteins or monoclonal antibodies, and are the desired product to be recovered.

The standing waves can be used to trap the cells and cell debris present in the cell culture media. The cells, having a positive contrast factor, move to the nodes (as opposed to the anti-nodes) of the standing wave. As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. Typical results published in literature state that the lateral force is two orders of magnitude smaller than the axial force. In contrast, the technology disclosed in this application provides for a lateral force to be of the same order of magnitude as the axial force.

The bioreactors of the present disclosure are designed to maintain a high intensity multi-dimensional acoustic standing wave. The device is driven by a function generator and amplifier (not shown). The device performance is monitored and controlled by a computer. It may be necessary, at times, due to acoustic streaming, to modulate the frequency or voltage amplitude of the standing wave. This may be done by amplitude modulation and/or by frequency modulation.

FIG. 1 illustrates a single standing wave system 100 that is comprised of a reflector plate 101 and an ultrasonic transducer 103 that is set to resonate so as to form a standing wave 102. Excitation frequencies typically in the range from hundreds of kHz to tens of MHz are applied by the transducer 103. One or more standing waves are created between the transducer 103 and the reflector 101. The standing wave is the sum of two propagating waves that are equal in frequency and intensity and that are traveling in opposite directions, i.e. from the transducer to the reflector and back. The propagating waves destructively interfere with each other and thus generate the standing wave. A dotted line 105 is used to indicate the amplitude. A node is a point where the wave has minimum amplitude, and is indicated with reference numeral 107. An anti-node is a point where the wave has maximum amplitude, and is indicated with reference numeral 109.

Figure 2:
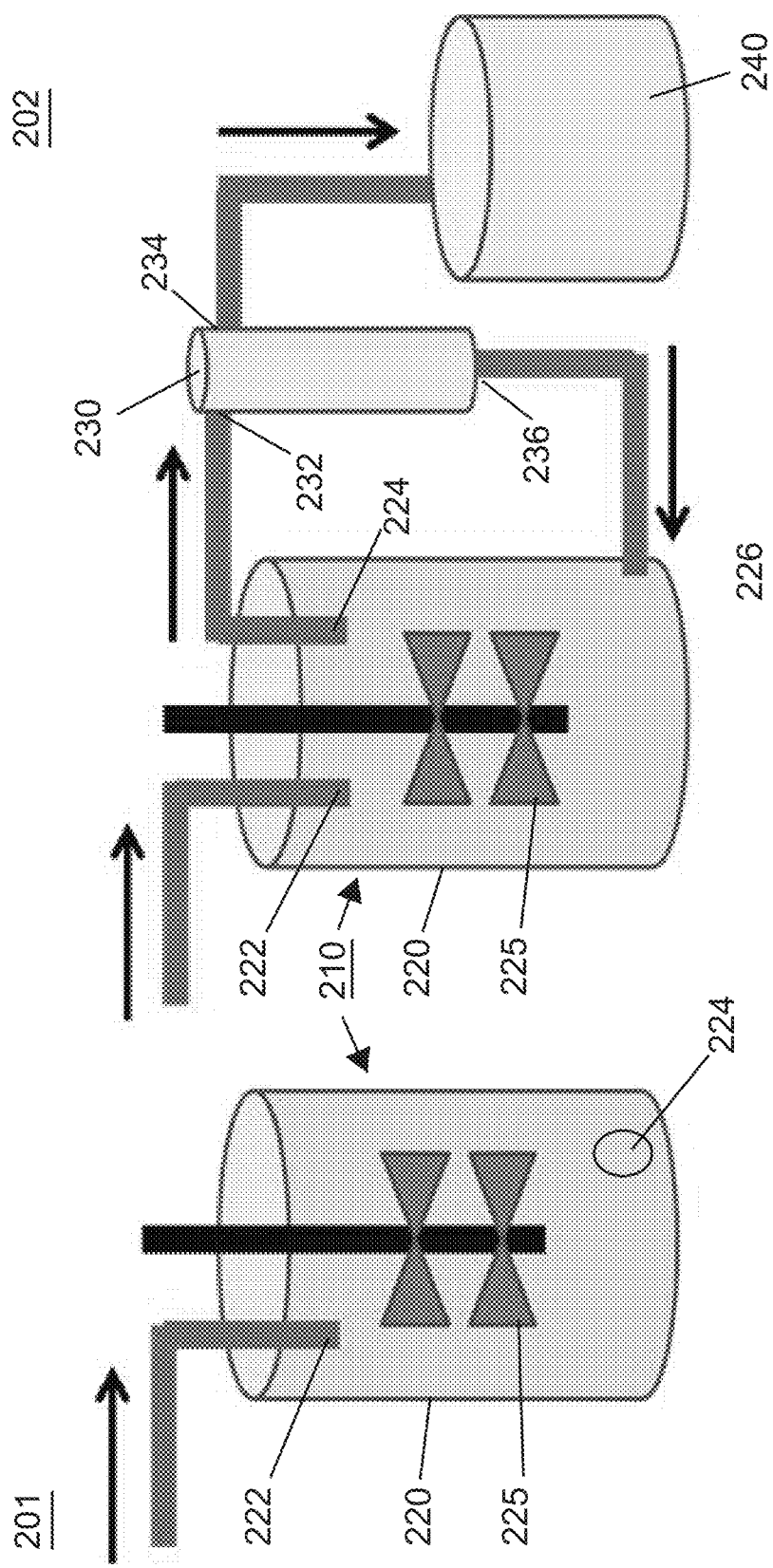
FIG. 2 is an illustration comparing a conventional fed-batch bioreactor system with a perfusion bioreactor system.

FIG. 2 is a schematic diagram that compares a conventional fed-batch bioreactor system 201 (left side) with a conventional perfusion bioreactor system 202 (right side). Beginning with the fed-batch bioreactor on the left, the bioreactor 210 includes a reaction vessel 220. The cell culture media is fed to the reaction vessel through a feed inlet 222. An agitator 225 is used to circulate the media throughout the cell culture. Here, the agitator is depicted as a set of rotating blades, though any type of system that causes circulation is contemplated. The bioreactor permits growth of a seed culture through a growth/production cycle, during which time debris, waste and unusable cells will accumulate in the bioreactor and the desired product (e.g. biomolecules such as monoclonal antibodies, recombinant proteins, hormones, etc.) will be produced as well. Due to this accumulation, the reaction vessel of a fed-batch process is typically much larger than that in a perfusion process. The desired product is then harvested at the end of the production cycle. The reaction vessel 220 also includes an outlet 224 for removing material.

Turning now to the perfusion bioreactor 202 on the right-hand side, again, the bioreactor includes a reaction vessel 220 with a feed inlet 222 for the cell culture media. An agitator 225 is used to circulate the media throughout the cell culture. An outlet 224 of the reaction vessel is fluidly connected to the inlet 232 of a filtering device 230, and continuously feeds the media (containing cells and desired product) to a filtering device. The filtering device is located downstream of the reaction vessel, and separates the desired product from the cells. The filtering device 230 has two separate outlets, a product outlet 234 and a recycle outlet 236. The product outlet 234 fluidly connects the filtering device 230 to a containment vessel 240 downstream of the filtering device, which receives a concentrated flow of the desired product (plus media) from the filtering device. From there, further processing/purification can occur to isolate/recover the desired product. The recycle outlet 236 fluidly connects the filtering device 230 back to a recycle inlet 226 of the reaction vessel 220, and is used to send the cells and cell culture media back into the reaction vessel for continued growth/production. Put another way, there is a fluid loop between the reaction vessel and the filtering device. The reaction vessel 220 in the perfusion bioreactor system 202 has a continuous throughput of product and thus can be made smaller. The filtering process is critical to the throughput of the perfusion bioreactor. A poor filtering process will allow for only low throughput and result in low yields of the desired product.

Figure 3:
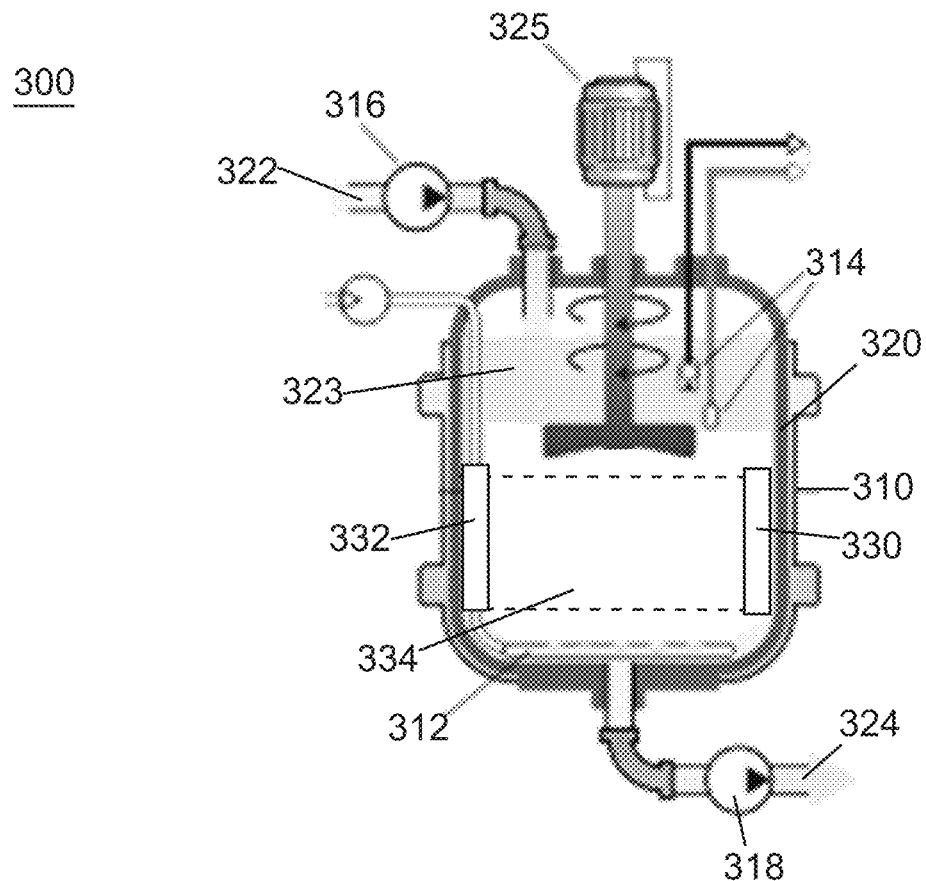
FIG. 3 is a cross-sectional view that shows the various components of a bioreactor of the present disclosure.

FIG. 3 is a cross-sectional view of a bioreactor 300 used in the systems of the present disclosure. As illustrated here, the bioreactor includes a reaction vessel 320 having an internal volume 323. A feed inlet 322 at the top of the vessel is used to feed a nutrient fluid stream into the vessel, and can also be used to feed in additional cells for maintaining the cell culture. An agitator 325 is present in the form of an impeller blade. An outlet 324 is shown at the bottom of the vessel. An aerator (not shown) can be used to provide gas to the internal volume. Sensors 314 are shown at the top right of the vessel. A pump 316 is illustrated for feeding the nutrient fluid stream into the vessel, as is another pump 318 for removing the nutrient fluid stream from the vessel. These pumps are used to circulate the nutrient fluid stream through the cell culture and furnish nutrition and oxygenation to keep the cells viable and productive. The pumps also deliver the produced biomolecules to another portion of the bioreactor (not shown) where these biomolecules can be further filtered and separated downstream of the reaction vessel.

The reaction vessel also includes an ultrasonic transducer 330 on one side of the vessel, and a reflector 332 located on another side opposite the ultrasonic transducer. A growth volume 334 is present between the transducer and the reflector (illustrated with dotted lines). A multi-dimensional standing wave (not shown) is generated between the transducer and the reflector that holds the cell culture in the growth volume. It is noted that the growth volume 334 is a portion of the internal volume 323. It is also noted that the blade of the agitator 325 is not located within the growth volume 334, because its presence can disrupt the standing wave A thermal jacket 310 surrounds the reaction vessel, and is used to regulate the temperature of the internal volume 323 and the cell culture. In this regard, it is usually desirable to maintain the temperature of the cell culture below 38° C. to prevent compromise of the cells. The thermal jacket is usually a chilling system used to mitigate any excess heat generated by the ultrasonic transducers. It is noted that the thermal jacket typically contains a temperature-regulating fluid. The standing wave created by the transducer 330 and reflector 332 can propagate through the jacket and the temperature-regulating fluid therein, and still continue to operate in the reaction vessel to hold the cell culture in place.

A secondary filtering system 312 is located between the growth volume 334 and the outlet 324. It is contemplated that in the event the standing waves fail to hold the cell culture in place, the secondary filtering system will operate to keep the cell culture within the reaction vessel and maintain their separation from the produced biomolecules. This could occur, for example, if a high percentage of the ultrasonic transducers fail, or if resonance is lost, or if the power is cut off to the reaction vessel.

During operation, the nutrient fluid stream is added into the reaction vessel through the feed inlet 322. The contents of the reaction vessel are mixed with the agitator 325. The desired product (e.g. biomolecules) is continuously produced by cells located within the growth volume 334, and are separated from the cell culture by the nutrient fluid steam flowing through the growth volume. The nutrient fluid stream, containing the biomolecular product, is drawn from the reaction vessel through outlet 324. From there, the nutrient fluid stream can be processed to isolate the desired product.

After processing, any cells and the nutrient fluid can be recycled back to the reaction vessel. In this regard, the present disclosure should not be construed as stating that no cells ever escape the standing wave and the growth volume.

It is noted that in FIG. 3, the reaction vessel inlet 322 is depicted at the top of the vessel and the outlet 324 is depicted at the bottom of the vessel. This arrangement can be reversed if desired, for example depending on the desired product to be obtained.

Figure 4:
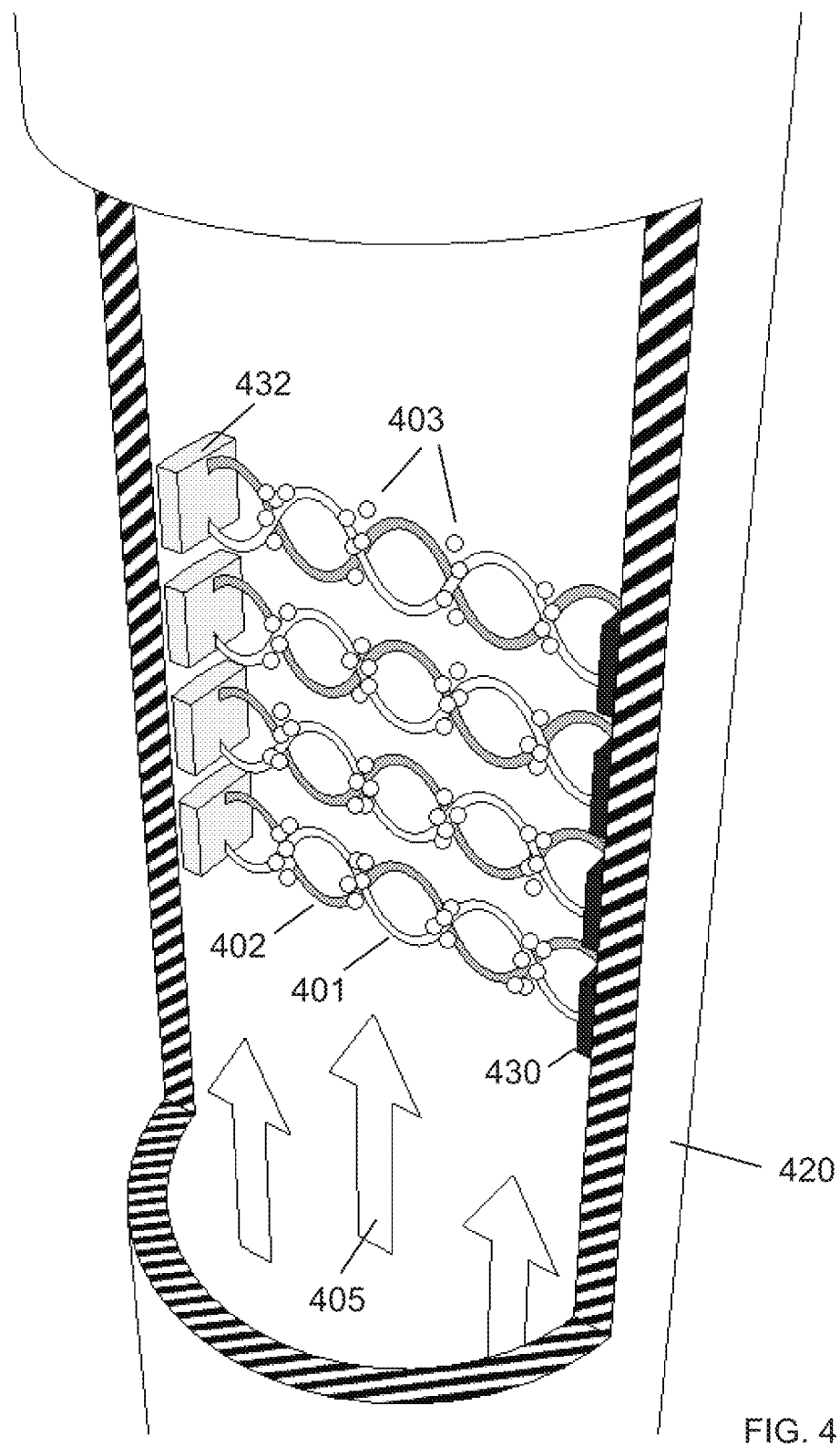
FIG. 4 is a cut-out view of a tubular bioreactor and the growth volume therein. A plurality of ultrasonic transducers is used to generate standing waves that hold a cell culture in place. Arrows illustrate an upward flow of a nutrient fluid stream through the standing waves and the cell culture held therein.

FIG. 4 is another illustration of the reaction vessel 420 of a bioreactor. Here, the reaction vessel is tubular, with the outlet at the top and the inlet at the bottom of the vessel, with fluid flow being indicated by arrows 405. An array of transducers 430 is arranged vertically on one side, and an array of reflectors 432 is arranged on an opposite side from the transducers. Waves 401 are transmitted from the transducer to the reflector, and waves 402 bounce back from the reflector to the transducer. The cell culture is held in place at the nodes of the standing wave thus generated, and is indicated with reference number 403.

The reaction vessel may be tubular, cubic, or another polygonal shape. The flow of the nutrient fluid stream through the reaction vessel of the bioreactor may be vertical, horizontal, or any angle in between. The combination of the ultrasonic transducers and the reflectors set up the resonant waves in the interior of the reaction vessel. The standing waves hold the cell culture at their net zero pressure nodes. The ultrasonic transducers and reflectors may be set perpendicular or at another angle to the fluid flow of the nutrient fluid stream through the acoustic bioreactor. This will allow for greater holding strength of the acoustic standing wave for the cell culture. The reflector may be a passive shape that is flat or is non-planar, or alternatively may itself be an active piezoelectric element that can change its shape to maintain resonance, but cannot itself generate an acoustic wave.

Figure 5:
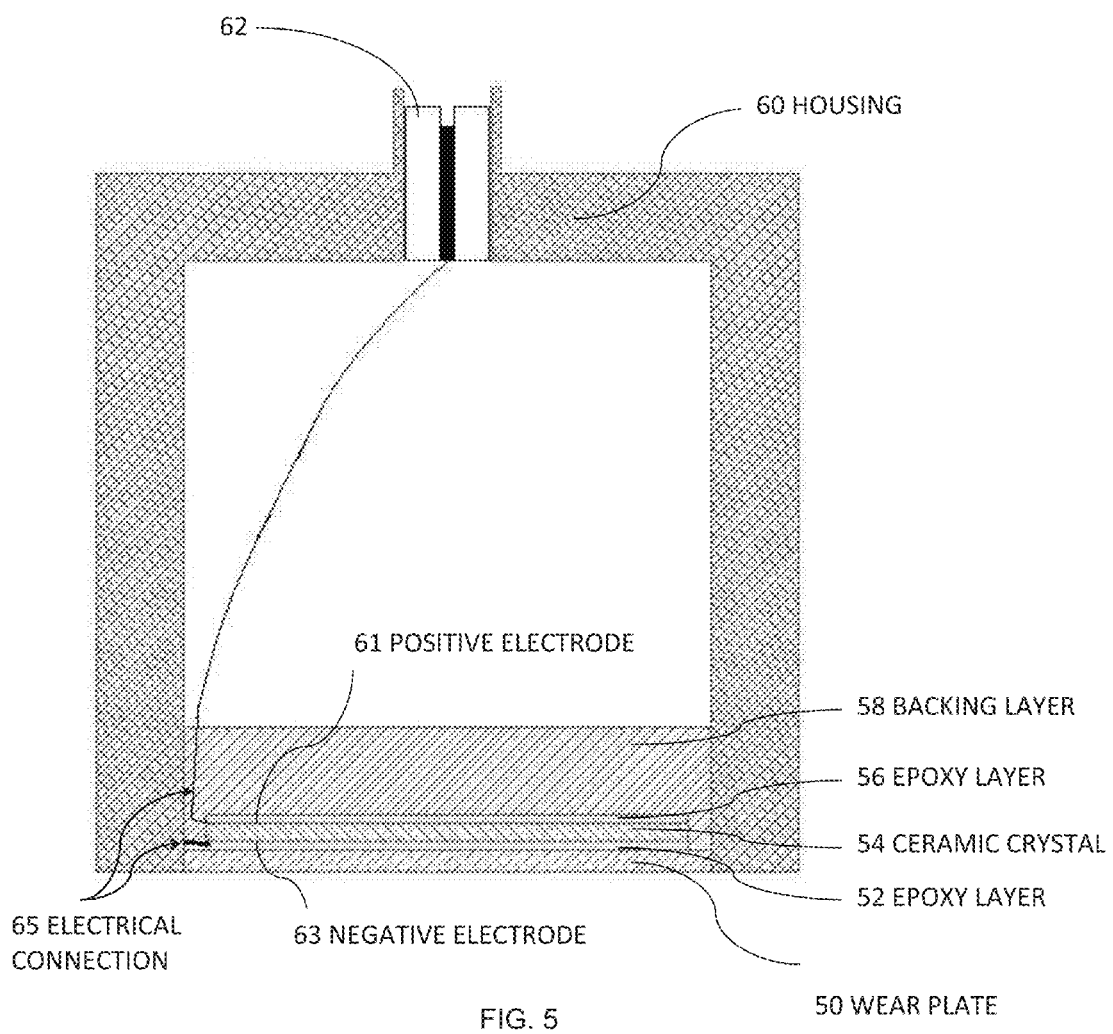
FIG. 5 is a cross-sectional diagram of a conventional ultrasonic transducer.
Figure 6:
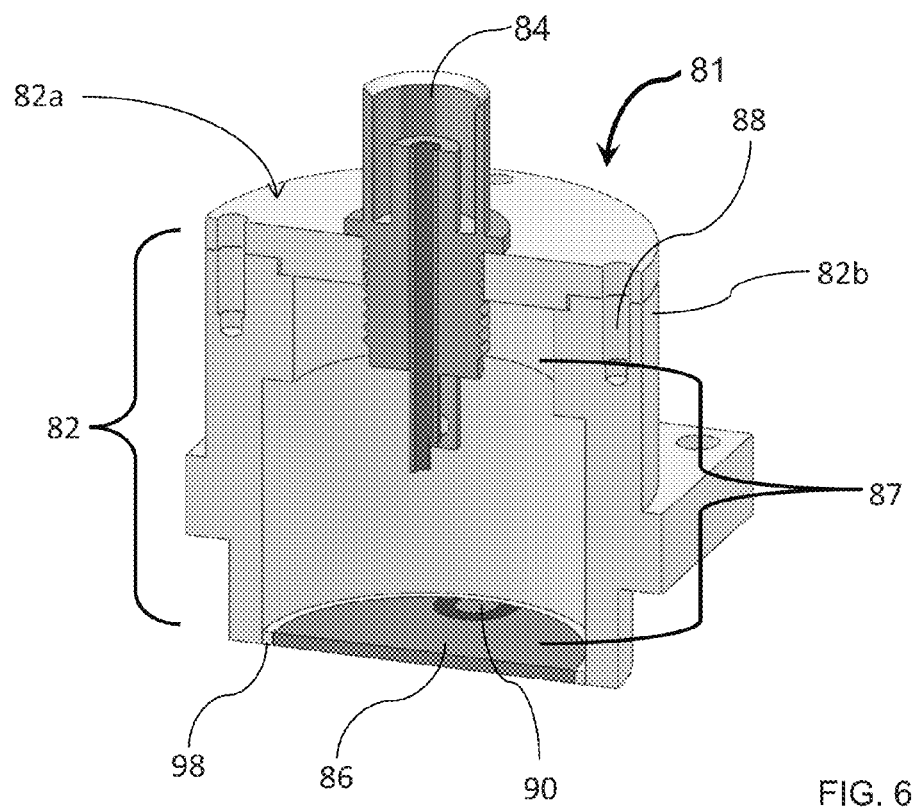
FIG. 6 is a cross-sectional diagram of an ultrasonic transducer of the present disclosure. An air gap is present within the transducer, and no backing layer or wear plate is present.
Figure 7:
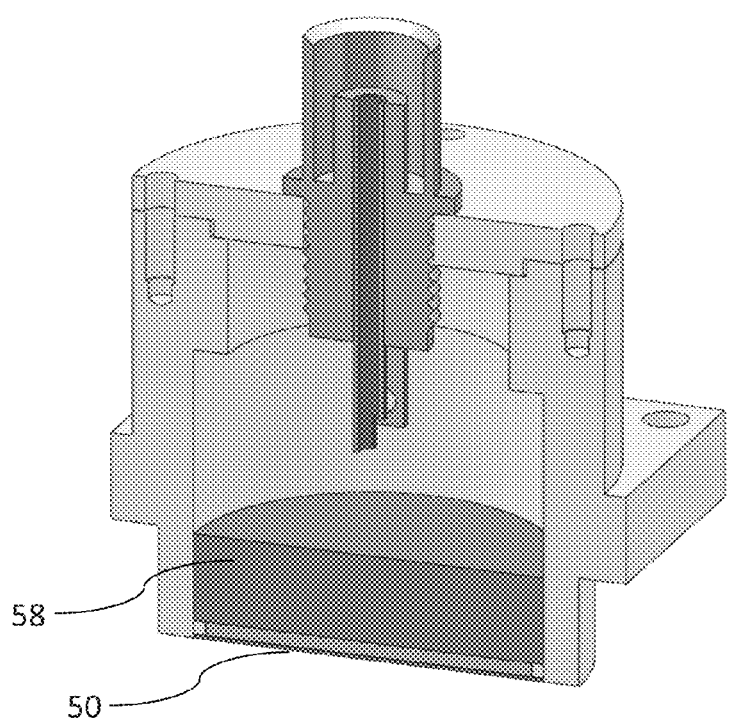
FIG. 7 is a cross-sectional diagram of an ultrasonic transducer of the present disclosure. An air gap is present within the transducer, and a backing layer and wear plate are present.

It may be helpful now to describe the ultrasonic transducer(s) used in the acoustophoretic filtering device in more detail. FIG. 5 is a cross-sectional diagram of a conventional ultrasonic transducer. This transducer has a wear plate 50 at a bottom end, epoxy layer 52, ceramic crystal 54 (made of, e.g. Lead Zirconate Titanate (PZT)), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates. However, the oscillating pressure and heating of the crystal can cause the wear plate to separate from the crystal.

Figure 8:
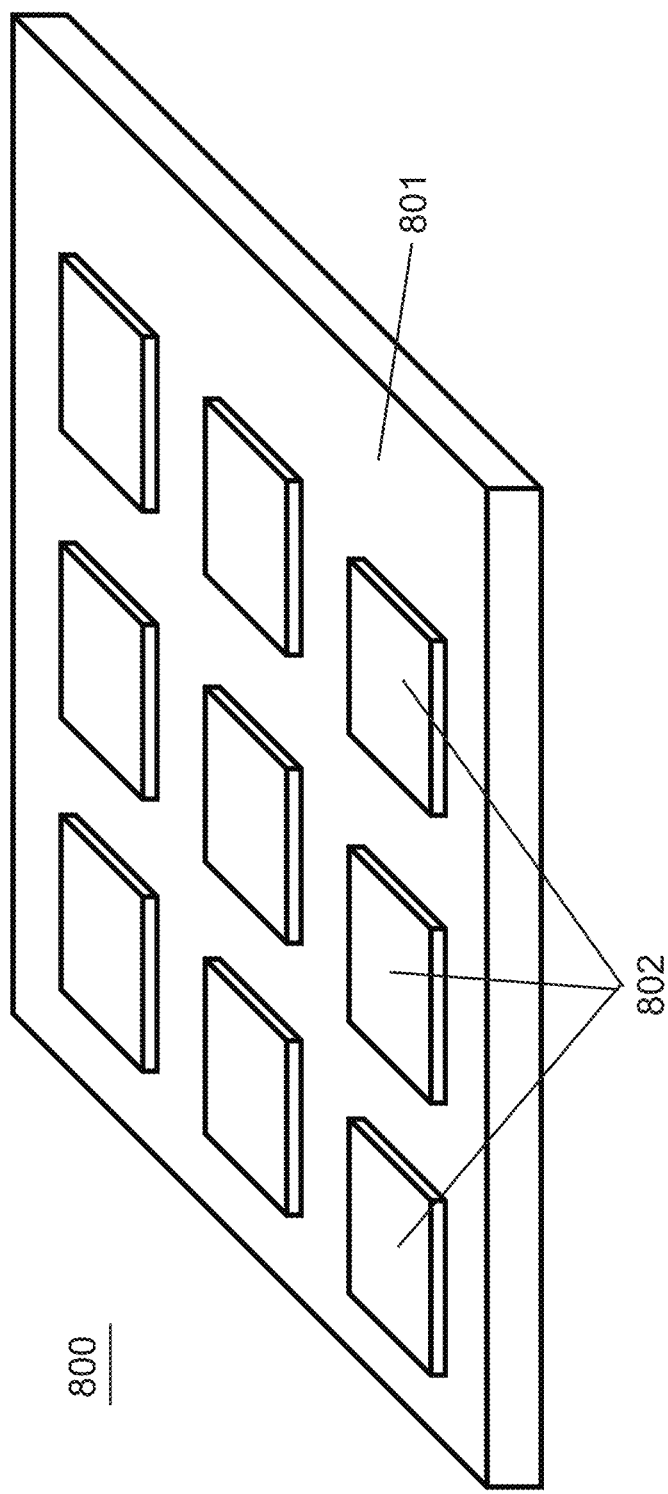
FIG. 8 is an illustration of a piezoelectric array that can be used to produce multi-dimensional standing waves.

FIG. 8 is a cross-sectional view of an ultrasonic transducer 81 of the present disclosure, which is used in the acoustophoretic filtering devices of the present disclosure. Transducer 81 has an aluminum housing 82. A PZT crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. The housing may also be composed of a more electrically conductive material, such as steel. The housing may also be grounded to the negative side of the transducer.

Figure 9:
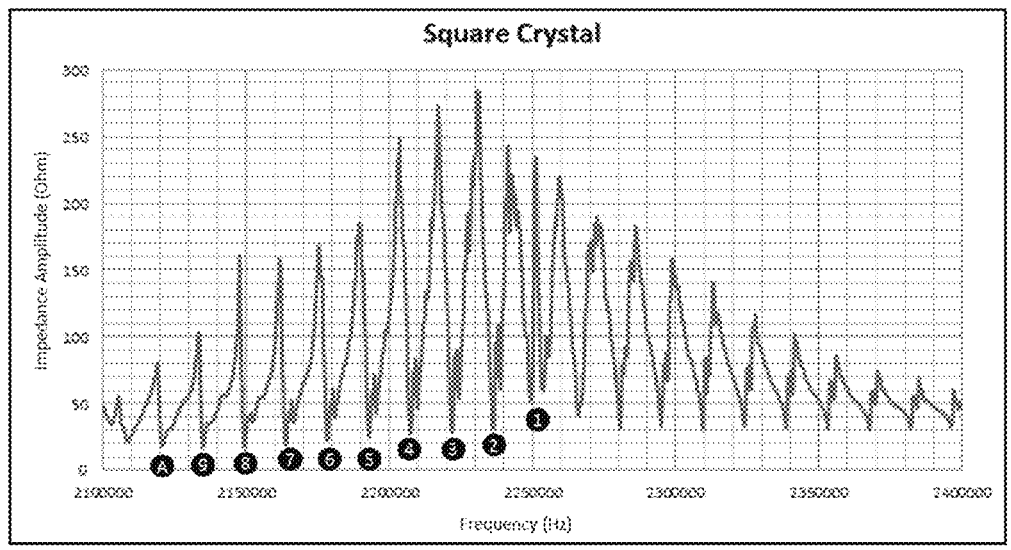
FIG. 9 is a graph of electrical impedance amplitude versus frequency for a square transducer driven at different frequencies.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 are each connected to an electrode (positive and negative), such as silver or nickel. A wrap-around electrode tab 90 connects to the bottom electrode and is isolated from the top electrode. Electrical power is provided to the PZT crystal 86 through the electrodes on the crystal, with the wrap-around tab 90 being the ground connection point. Note that the crystal 86 has no backing layer or epoxy layer as is present in FIG. 5. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 9.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

In some embodiments, the ultrasonic transducer has a 1 inch diameter and a nominal 2 MHz resonance frequency. Each transducer can consume about 28 W of power for droplet trapping at a flow rate of 3 GPM. This translates to an energy cost of 0.25 kW hr/m$^3$. This is an indication of the very low cost of energy of this technology. Desirably, each transducer is powered and controlled by its own amplifier. In other embodiments, the ultrasonic transducer uses a square crystal, for example with 1"×1" dimensions. Alternatively, the ultrasonic transducer can use a rectangular crystal, for example with 1"×2.5" dimensions. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W.

The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired three-dimensional acoustic standing wave patterns.

FIG. 8 is an illustration of a piezoelectric ultrasonic transducer 800 that may also be utilized to generate multiple standing waves. The base 801 of the transducer has an array formed from multiple piezoelectric elements 802 on the surface. These piezoelectric elements may be formed on the surface in a variety of ways, including adhesion of piezoelectric crystals, photomasking and deposition techniques such as those utilized in the electronic industry. For example, the surface of a piezoelectric crystal can be cut in a pattern to a certain depth, and the cut-away areas are then filled with a secondary material to isolate the individual areas to form the resulting pattern on the piezoelectric crystal surface.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more trapping locations for the cells/biomolecules. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 9, were used as excitation frequencies. The conditions were experiment duration of 30 min, a 1000 ppm oil concentration of approximately 5-micron SAE-30 oil droplets, a flow rate of 500 ml/min, and an applied power of 20 W. Oil droplets were used because oil is denser than water, and can be separated from water using acoustophoresis.

FIG. 9 shows the measured electrical impedance amplitude of a square transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

Figure 10:
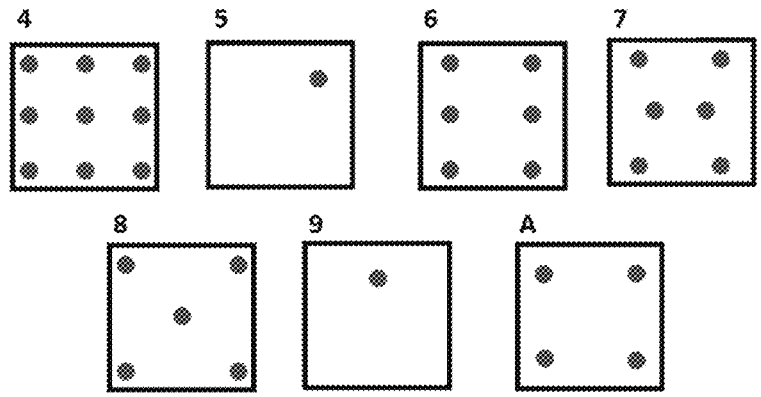
FIG. 10 illustrates the trapping line configurations for seven of the peak amplitudes of FIG. 9 from the direction orthogonal to fluid flow.

As the oil-water emulsion passed by the transducer, the trapping lines of oil droplets were observed and characterized. The characterization involved the observation and pattern of the number of trapping lines across the fluid channel, as shown in FIG. 10, for seven of the ten resonance frequencies identified in FIG. 9. Different displacement profiles of the transducer can produce different (more) trapping lines in the standing waves, with more gradients in displacement profile generally creating higher trapping forces and more trapping lines.

Figure 11:
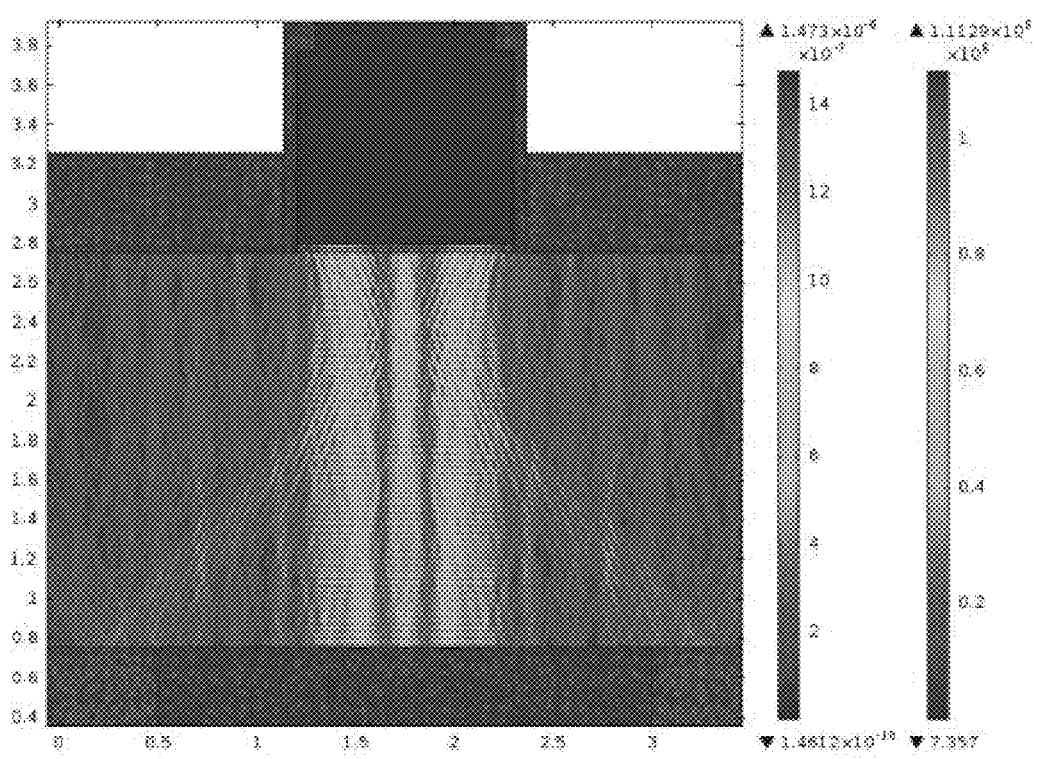
FIG. 11 is a computer simulation of the acoustic pressure amplitude (right-hand scale in Pa) and transducer out of plane displacement (left-hand scale in meters). The text at the top of the left-hand scale reads "$\times 10^{-7}$". The text at the top of the left-hand scale by the upward-pointing triangle reads "$1.473 \times 10^{-6}$". The text at the bottom of the left-hand scale by the downward-pointing triangle reads "$1.4612 \times 10^{-10}$". The text at the top of the right-hand scale reads "$\times 10^{6}$". The text at the top of the right-hand scale by the upward-pointing triangle reads "$1.1129 \times 10^{6}$". The text at the bottom of the right-hand scale by the downward-pointing triangle reads "7.357". The triangles show the maximum and minimum values depicted in this figure for the given scale. The horizontal axis is the location within the chamber along the X-axis, in inches, and the vertical axis is the location within the chamber along the Y-axis, in inches.

FIG. 11 is a numerical model showing a pressure field that matches the 9 trapping line pattern. The numerical model is a two-dimensional model; and therefore only three trapping lines are observed. Two more sets of three trapping lines exist in the third dimension perpendicular to the plane of the page.

In the present systems, the system is operated at a voltage and frequency such that the cells (that make up the cell culture) are trapped by the ultrasonic standing wave, i.e., remain in a stationary position. The cells are collected along well-defined trapping lines, separated by half a wavelength. Within each nodal plane, the cells are trapped in the minima of the acoustic radiation potential. The axial component of the acoustic radiation force drives cells with a positive contrast factor to the pressure nodal planes, whereas cells with a negative contrast factor are driven to the pressure anti-nodal planes. The radial or lateral component of the acoustic radiation force is the force that traps the cell. It therefore must be larger than the combined effect of fluid drag force and gravitational force. In systems using typical transducers, the radial or lateral component of the acoustic radiation force is typically several orders of magnitude smaller than the axial component of the acoustic radiation force. However, the lateral force generated by the transducers of the present disclosure can be significant, on the same order of magnitude as the axial force component, and is sufficient to overcome the fluid drag force at linear velocities of up to 1 cm/s.

The lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e. the air gap within the transducer) and on the other side by the fluid of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 12:
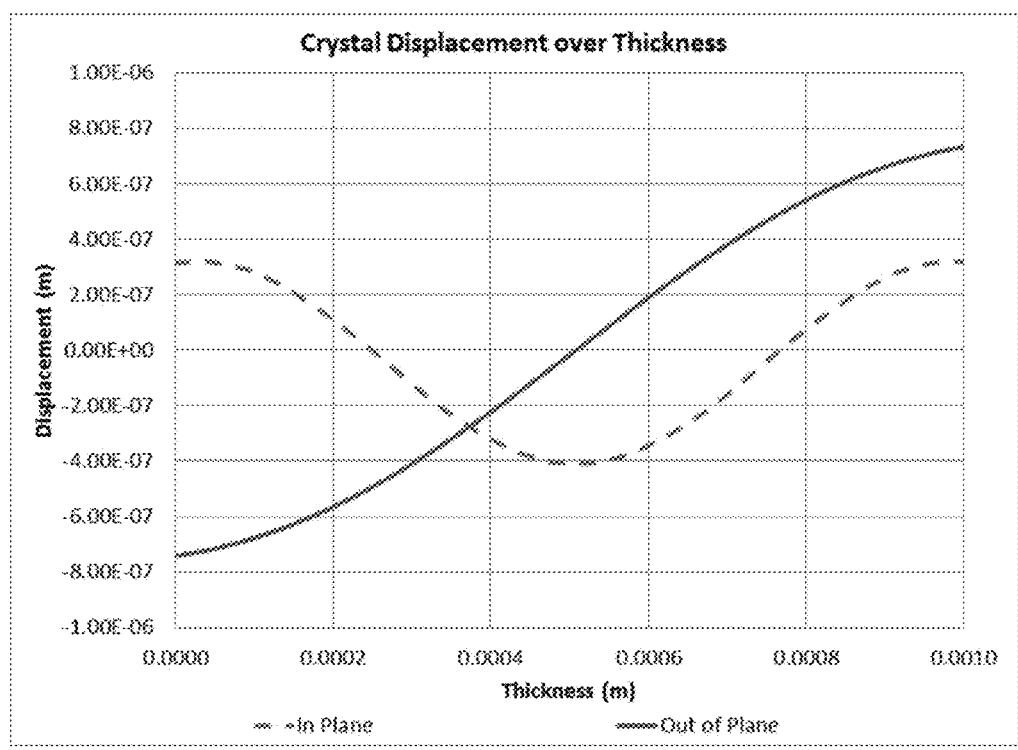
FIG. 12 shows the In-Plane and Out-of-Plane displacement of a crystal where composite waves are present.

FIG. 12 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation as described in FIG. 14. The maximum number of m and n is a function of the dimension of the crystal and the frequency of excitation.

The transducers are driven so that the piezoelectric crystal vibrates in higher order modes of the general formula (m, n), where m and n are independently 1 or greater. Generally, the transducers will vibrate in higher order modes than (2,2). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction. Put another way, driving the transducers to generate multi-modal vibrations can generate multiple standing waves from one piezoelectric crystal.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming. Again, the transducer is usually operated so that the acoustic standing wave remains on resonance. A feedback system is generally present for this purpose.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer and the reflector. Hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

Figure 13:
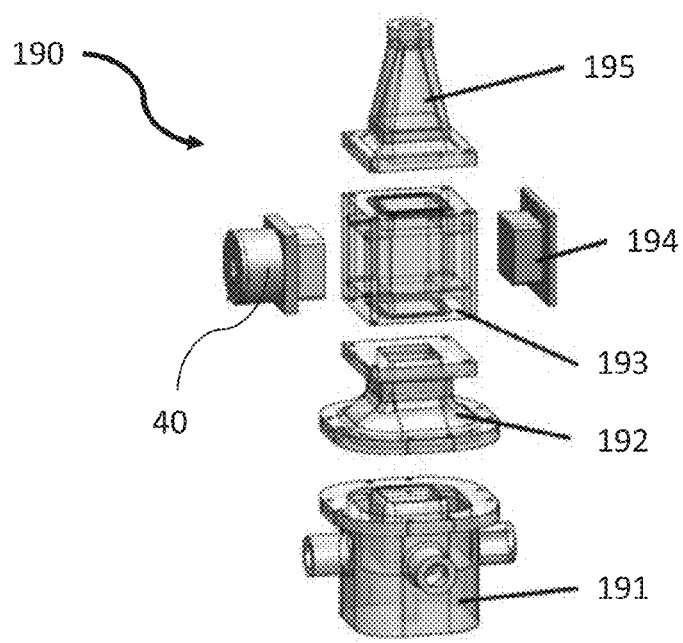
FIG. 13 shows an exploded view of a bioreactor that can be used, having one growth volume.
Figure 14:
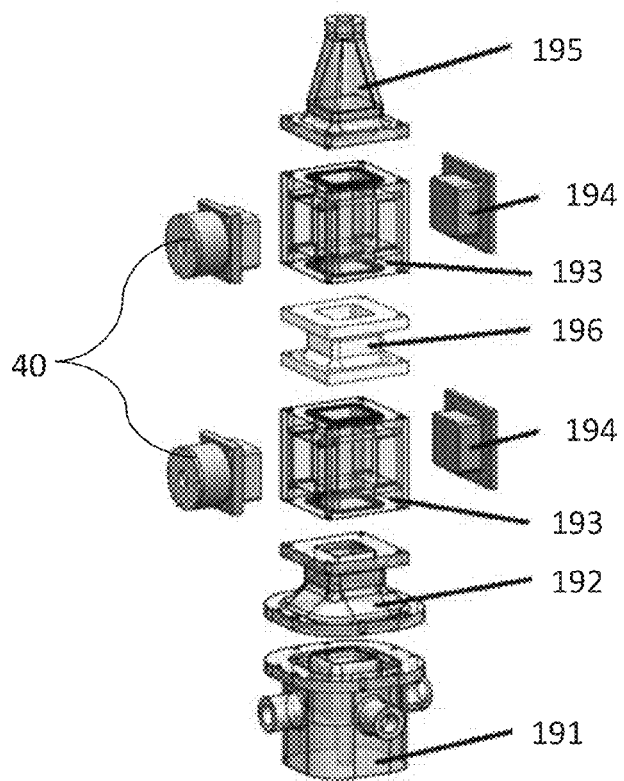
FIG. 14 shows an exploded view of a bioreactor having two stacked growth volumes.

FIG. 13 and FIG. 14 are exploded views showing the various parts of a reaction vessel that uses acoustophoresis to hold cells in place in a growth volume. FIG. 15 provides only one chamber for one growth volume, while FIG. 16 has two chambers and can have two different growth volumes.

Referring to FIG. 13, fluid enters the reaction vessel 190 through a four-port inlet 191. A transition piece 192 is provided to create plug flow through the chamber 193. A transducer 40 and a reflector 194 are located on opposite walls of the chamber for holding the cell culture in place. Fluid then exits the chamber 193 and the reaction vessel through outlet 195. The growth volume is located in chamber 193.

FIG. 14 has two chambers 193. A system coupler 196 is placed between the two chambers 193 to join them together. A growth volume can be located in each chamber 193.

In biological applications, it is contemplated that all of the parts of the system (e.g. the reaction vessel, tubing leading to and from the bioreactor, the temperature-regulating jacket, etc.) can be separated from each other and be disposable. Avoiding centrifuges and filters allows better separation of the CHO cells without lowering the viability of the cells. The frequency of the transducers may also be varied to obtain optimal effectiveness for a given power.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A process for collecting biomolecules from a cell culture, comprising:
suspending the cell culture in a growth volume of a bioreactor, the bioreactor including at least one ultrasonic transducer and a reflector located opposite the at least one ultrasonic transducer, each ultrasonic transducer being driven to produce a multi-dimensional acoustic standing wave that holds the cell culture in the growth volume; and
flowing a nutrient fluid stream through the cell culture to collect the biomolecules.

2. The process of claim 1, wherein the bioreactor further comprises a secondary filtering system located between the growth volume and a bioreactor outlet.

3. The process of claim 2, further comprising activating the secondary filtering system if the multi-dimensional acoustic standing wave fails.

4. The process of claim 1, wherein the multi-dimensional acoustic standing wave is in resonance.

5. The process of claim 1, wherein the at least one ultrasonic transducer is an array of elements.

6. The process of claim 1, wherein each ultrasonic transducer produces a plurality of multi-dimensional acoustic standing waves.

7. The process of claim 1, wherein the bioreactor does not include an impeller within the growth volume.

8. The process of claim 1, wherein the cell culture is composed of Chinese hamster ovary (CHO) cells.

9. The process of claim 1, wherein the biomolecules are monoclonal antibodies or recombinant proteins.

10. The process of claim 1, wherein the multi-dimensional acoustic standing wave has an axial force component and a lateral force component which are of the same order of magnitude.

11. The process of claim 1, wherein the ultrasonic transducer comprises a piezoelectric material that can vibrate in a higher order mode shape.

12. The process of claim 11, wherein the piezoelectric material has a rectangular shape.

13. The process of claim 1, wherein the ultrasonic transducer comprises:
a housing having a top end, a bottom end, and an interior volume; and
a crystal at the bottom end of the housing having an exposed exterior surface and an interior surface, the crystal being able to vibrate when driven by a voltage signal.

14. The process of claim 13, wherein a backing layer contacts the interior surface of the crystal, the backing layer being made of a substantially acoustically transparent material.

15. The process of claim 14, wherein the substantially acoustically transparent material is balsa wood, cork, or foam.

16. The process of claim 14, wherein the substantially acoustically transparent material has a thickness of up to 1 inch.

17. The process of claim 14, wherein the substantially acoustically transparent material is in the form of a lattice.

18. The process of claim 13, wherein an exterior surface of the crystal is covered by a wear surface material with a thickness of a half wavelength or less, the wear surface material being a urethane, epoxy, or silicone coating, or being made of aluminum oxide.

19. The process of claim 13, wherein the crystal has no backing layer or wear layer.

20. The process of claim 1, wherein the multi-dimensional acoustic standing wave is a three-dimensional standing wave.

* * * * *